United States Patent [19]

Maryanoff

[11] Patent Number: 5,258,402
[45] Date of Patent: Nov. 2, 1993

[54] IMIDATE DERIVATIVES OF PHARMACEUTICALLY USEFUL ANTICONVULSANT SULFAMATES

[75] Inventor: Bruce E. Maryanoff, New Hope, Pa.

[73] Assignee: McNeil-PPC, Inc., Milltown, N.J.

[21] Appl. No.: 896,936

[22] Filed: Jun. 11, 1992

[51] Int. Cl.$^5$ .................. A61K 31/35; C07D 311/78
[52] U.S. Cl. ................................. 514/454; 549/387; 549/338; 549/31
[58] Field of Search ............... 549/387, 338; 514/454

*Primary Examiner*—Nicky Chan
*Attorney, Agent, or Firm*—Ralph R. Palo

[57] ABSTRACT

Imidate derivatives of sulfamates having the following formula (I):

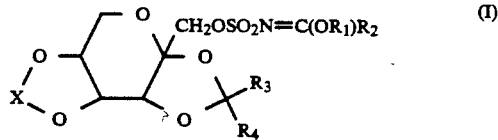

wherein $R_1$, $R_2$, $R_3$, $R_4$ and X are as herein defined have been found to be useful prodrug and exhibit anticonvulsant activity when converted to the active agent upon administration to a mammal and are thus useful in the treatment of conditions such as epilepsy. Further, the present invention encompasses pharmaceutical compositions containing a compound of formula (I) as well as methods for their use.

14 Claims, No Drawings

IMIDATE DERIVATIVES OF PHARMACEUTICALLY USEFUL ANTICONVULSANT SULFAMATES

BACKGROUND OF THE INVENTION

Sulfamates of various structures, including those derived from monosaccharides, are described in *J. Med. Chem.* 1987, 30, 880 and in U.S. Pat. No. 4,075,351. Certain of these sulfamates are useful as pharmaceutical agents. More recently, sulfamates having various pharmaceutical activity in the areas of epilepsy, glaucoma, peptic ulcers, and male infertility are described in U.S. Pat. Nos. 4,513,006, 4,459,601 and 4,792,569. One of the compounds covered by U.S. Pat. No. 4,513,006, topiramate, has not only been found to exhibit particularly significant anticonvulsant activity in animals, but also appears to be useful in humans for the treatment of epilepsy (see *Drugs Future*, 1989, 14, 342). Still other related sulfamates are disclosed in a recently filed application (Ser. No. 07/874,875) by the same assignee as the present invention, which application was filed on Apr. 28, 1992.

While sulfamate compounds of the type disclosed in U.S. Pat. No. 4,513,006 have been shown to exhibit useful biological activity when administered to mammals, improved activity is desirable.

Accordingly, it is one of the objects of the present invention to describe novel derivatives of the sulfamate compounds of the type disclosed in U.S. Pat. No. 4,513,006 in which the sulfamate portion is masked by an imidate group that can be removed in a physiological milieu to generate the parent drug (See *J. Med. Chem.* 1988, 31, 2066). Such derivatives, known commonly as prodrugs, could afford improved biological activity or properties upon administration to mammals.

SUMMARY OF THE INVENTION

It has been found that certain imidate derivatives of sulfamates, having the formula (I):

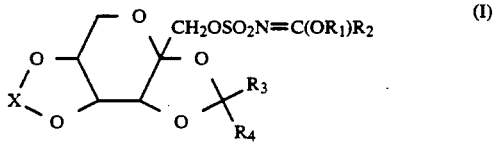

wherein $R_1$, $R_2$, $R_3$, $R_4$ and X are as defined hereinafter exhibit anticonvulsant activity upon conversion to the active agent. Such compounds are prodrugs for the active agent by virtue of their hydrolysis in vivo. Derivatization of the antiepileptic drug topiramate, and its congeners, gives rise to these imidate prodrugs that afford anticonvulsant activity upon administration to a mammal, and are thus useful for the treatment of epilepsy. Such prodrugs may be superior to the parent compound in their absorption and distribution within mammals. These prodrugs may also be useful for the treatment of glaucoma, peptic ulcers, hypertension, congestive heart failure and other types of edema.

DETAILED DESCRIPTION OF THE INVENTION

More particularly, the present invention is directed to imidate derivatives of the following formula (I):

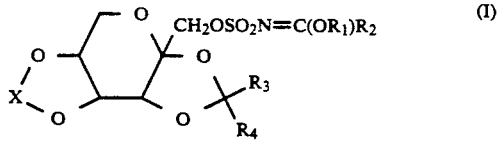

$R_1$ is $C_1-C_{10}$ alkyl or $C_3-C_{10}$ cycloalkyl.

$R_2$ is hydrogen, $C_1-C_{10}$, alkyl, $C_1-C_6$ alkoxy, $C_3-C_{10}$ cycloalkyl, or phenyl.

$R_3$ and $R_4$ are the same or different and are selected from any of hydrogen, $C_1-C_6$ alkyl, or are taken together to form a cyclopentyl or cyclohexyl ring. More preferably, $R_3$ and $R_4$ are either H or $C_1-C_2$ alkyl.

X is $CR_5R_6$, where $R_5$ and $R_6$ are the same or different and are selected from any of hydrogen, $C_1-C_6$ alkyl, or $C_1-C_4$ perfluoroalkyl, or are taken together to form a cyclopentyl or cyclohexyl ring; or X is $S(R_7)_n(R_8)_p$, where $R_7$ and $R_8$ are the same or different and are selected from either oxygen or $NR_9$, where $R_9$ is selected from any of hydrogen, $C_1-C_4$ alkyl, $C_1-C_4$ perfluoroalkyl, arenesulfonyl, $C_1$ to $C_4$ alkoxycarbonyl, or benzyloxycarbonyl. Preferably $R_7$ and $R_8$ are each O.

Each of p and n is either zero or one, with the proviso that n and p are not both equal to zero at the same time. A lone pair of electrons is designated when either n or p are equal to zero. More preferably, when X is $CR_5R_6$, $R_5$ and $R_6$ are hydrogen or $C_1-C_3$ alkyl and, when X is $S(R_7)_n(R_8)_p$, $R_7$ and $R_8$ are both oxygen and n and p equal one.

As used herein alkyl and alkoxy include straight and branched chains. For example, alkyl radicals include methyl, ethyl, propyl, isopropyl, n-butyl, isobutyl, sec-butyl, t-butyl, n-pentyl, 2-methyl-3-butyl, 1-methylbutyl, 2-methylbutyl, neopentyl, n-hexyl, 1-methylpentyl and 3-methylpentyl. Perfluoroalkyl radicals are defined as the previously described straight or branched chain alkyl radicals in which all of the hydrogen atoms have been replaced with fluorine atoms; e.g., trifluoromethyl, pentafluoroethyl, heptafluoropropyl, etc. Alkoxy radicals are oxygen ethers formed from the previously described straight or branched chain alkyl groups.

Arenesulfonyl radicals include, for example, phenylsulfonyl, o-toluenesulfonyl, m-toluenesulfonyl, p-toluenesulfonyl ("Ts"), 1-naphthalenesulfonyl, 2-naphthalenesulfonyl, and 5-dimethylamino-1-naphthalenesulfonyl.

Cyclic sulfites are designated when n equals one, p equals zero, and $R_7$ is oxygen and also when n equals zero, p equals one and $R_8$ is oxygen. Cyclic sulfates are designated when n equals one, p equals one, $R_7$ is oxygen and $R_8$ is oxygen. Cyclic imidosulfites are designated when n equals one, p equals zero and $R_7$ is $NR_9$ and also when n equals zero and p equals one and $R_8$ is $NR_9$. Cyclic imidosulfates are designated when n equals one, p equals one, $R_7$ is oxygen and $R_8$ is $NR_9$ and also when n equals one, p equals one, $R_7$ is $NR_7$ and $R_8$ is oxygen. Cyclic diimidosulfates are designated when n equals one, p equals one, $R_7$ equals $NR_9$ and $R_8$ equals $NR_9$.

The compounds of this invention include the various individual anomers, diastereomers and enantiomers as well as mixtures thereof. Compounds may exist in the $\beta$-D-fructopyranose and $\beta$-L-fructopyranose absolute configurations. Preferably, the oxygens connected to the pyran ring in formula (I) are in the $\beta$-D-fructopyranose configuration. Such compounds are included within the definition of formula (I).

As used herein, the β-D-fructopyranose absolute configuration is defined as:

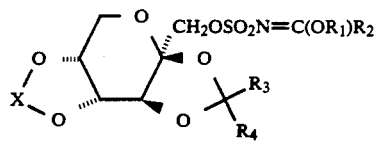

and the β-L-fructopyranose absolute configuration is defined as:

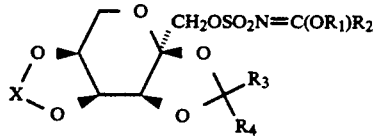

The compounds of formula (I) may be synthesized by heating the corresponding sulfamate drug of Formula (II) with ortho ester or ortho carbonate reagents such as HC(OMe)$_3$, (EtO)$_4$C, PhC(OMe)$_3$ and MeC(OEt)$_3$, used in substantial stoichiometric excess, at a temperature of about 50°-150° C., usually in the absence of a solvent (although inert solvents, such as toluene, dichloroethane, 1,2-dichlorobenzene, and the like can be used). As used herein Et means ethyl and Me means methyl. The product is then isolated by standard methods, such as crystallization or chromatography (preferably in the absence of water to avoid hydrolysis of the imidate group).

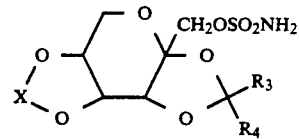

When X is CR$_5$R$_6$, the corresponding sulfamate drug is represented by the general formula (IIa):

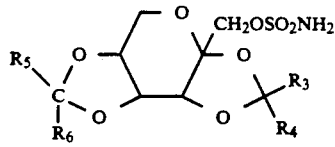

wherein R$_3$, R$_4$, R$_5$, and R$_6$ are as defined previously herein.

When X is S(R$_7$)$_n$(R$_8$)$_p$, the corresponding sulfamate drug is represented by the general formula (IIb):

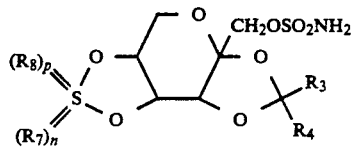

wherein R$_3$, R$_4$, R$_7$, R$_8$, n and p are as defined previously herein.

The compound of the formula (IIa) may be synthesized according to the procedures recited in U.S. Pat. Nos. 4,513,006, 4,582,416 which are incorporated by reference herein.

The compounds of the formula (IIb) may be synthesized by any of the methods recited hereinafter.

In the first method, a compound of the formula (III);

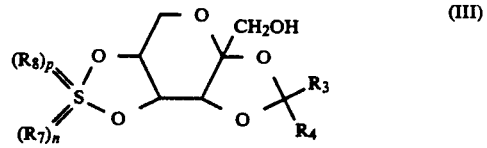

is reacted with sulfamoyl chloride (formula Cl-SO$_2$NH$_2$), in the presence of a base such as potassium t-butoxide, sodium hydride, triethylamine, or pyridine at a temperature of about −60° to about 25° C. in an aprotic solvent such as toluene, ethyl acetate, tetrahydrofuran, acetonitrile or dimethylformamide thereby producing the compound of formula (IIb). For example:

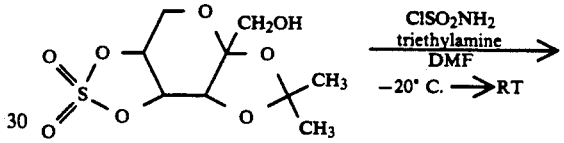

In a second method to produce compounds of formula (IIb), a compound of formula (III) is reacted with sulfuryl chloride in the presence of pyridine or triethylamine at a temperature of about −60° to about 25° C. in an aprotic solvent such as diethyl ether, ethyl acetate, dichloromethane or toluene to produce a chlorosulfate of the formula (IV).

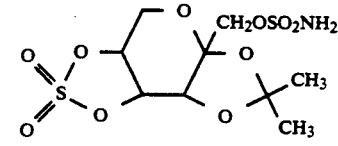

The chlorosulfate of formula (IV) is subsequently reacted with ammonia, under anhydrous conditions, at a temperature of about −60° to about 25° C. in an aprotic solvent such as tetrahydrofuran, acetonitrile or dichloromethane to produce a compound of formula (IIb). For example:

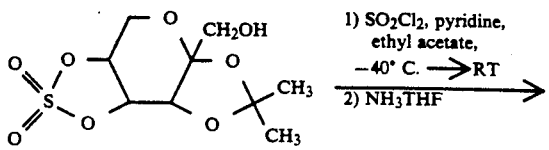

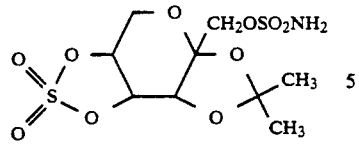

A third method to produce compounds of formula (IIb) involves reacting a diol of the formula (V):

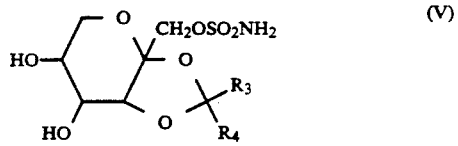

with sulfuryl chloride in the presence of pyridine or triethylamine at a temperature of about −78° to about 25° C. in an aprotic solvent such as ethyl acetate, toluene, or dichloromethane to produce the bis-chlorosulfate of formula (VI).

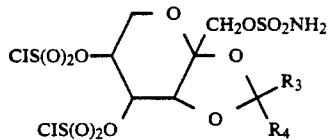

For example:

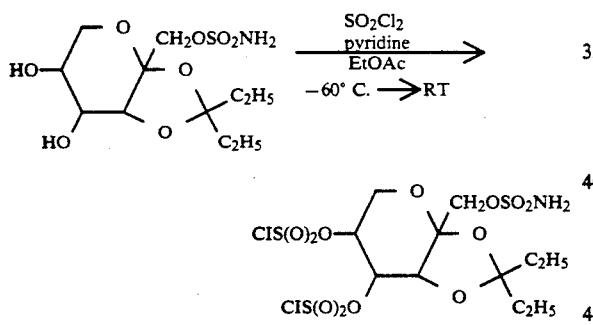

Dechlorosulfation of the bis-chlorosulfate of formula (VI) with a weak base such as NaHCO₃ or pyridine in an alcohol such as methanol or ethanol at about −40° to about 25° C. yields cyclic sulfate compounds of the formula (IIb). For example:

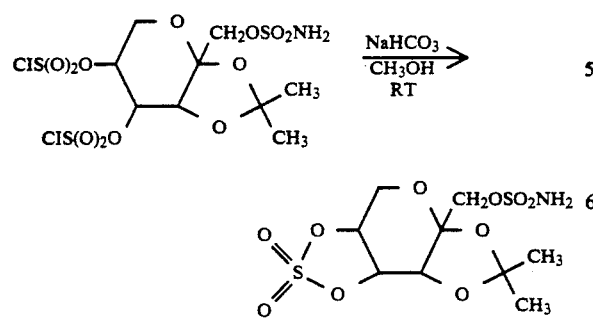

A method to prepare cyclic sulfate and imidosulfate compounds of the formula (IIb) involves the oxidation of the corresponding cyclic sulfites or imidosulfites of the formula (I) with RuCl₃ and NaIO₄ according to the method of Sharpless et al. in *Tetrahedron Lett.* 1989, 30, 655. For example:

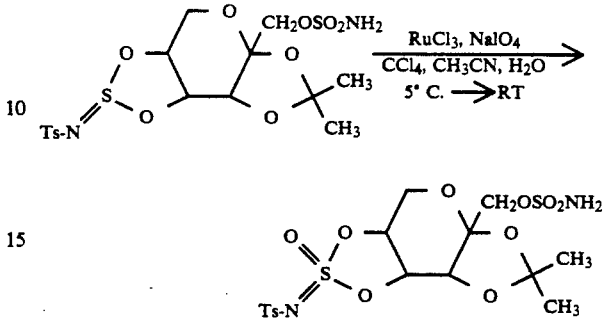

(Where Ts is defined as p-toluenesulfonyl)

Other strong oxidants, such as OsO₄, KMnO₄, dialkyl dioxiranes, diperfluoroalkyl dioxiranes or alkylperfluoroalkyl dioxiranes may also be used to affect this transformation. For example:

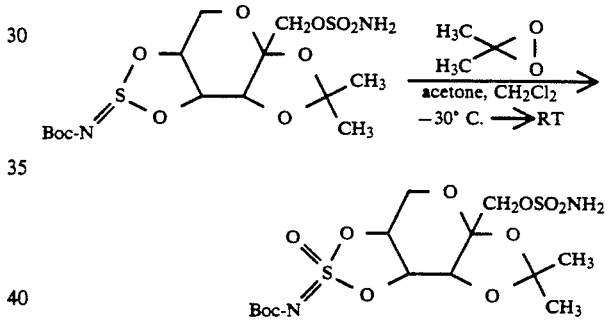

(Where Boc is defined as t-butoxycarbonyl)

Cyclic sulfate and imidosulfate compounds of formula (IIb) may also be prepared from benzyl cyclic sulfites and imidosulfites of the formula (VII).

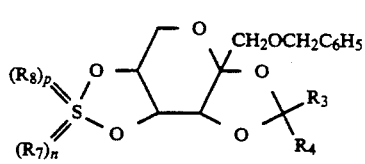

Oxidation of cyclic sulfites and imidosulfites of formula (VII) with RuO₄ or other strong oxidants produces the corresponding benzyl cyclic sulfates and imidosulfates. Debenzylation of these benzyl cyclic sulfates and imidosulfates to the corresponding cyclic sulfates and imidosulfates of the formula (III) can be effected with hydrogen in the presence of a noble metal catalyst, such as Pd(OH)₂ on carbon, in an alcoholic solvent such as ethanol or methanol at about 25° to about 60° C.

For example:

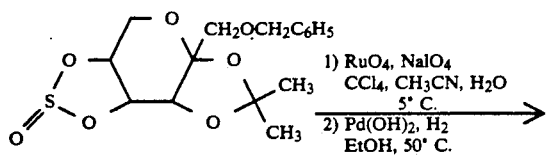

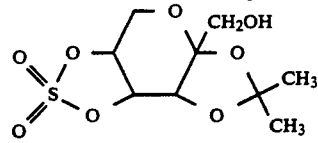

Conversion of the resulting compounds of the formula (III) to the corresponding compounds of formula (IIb) may be accomplished as previously described herein.

Alternatively, benzyl cyclic sulfates and diimidosulfates of the formula (VII) may be prepared by the treatment of diols of formula (VIII) with an excess of sodium hydride in tetrahydrofuran at room temperature followed by reaction with sulfuryldiimidazole or NR7-substituted diimidosulfuryl fluorides, respectively.

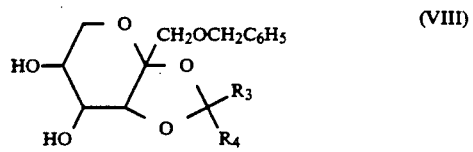

For example:

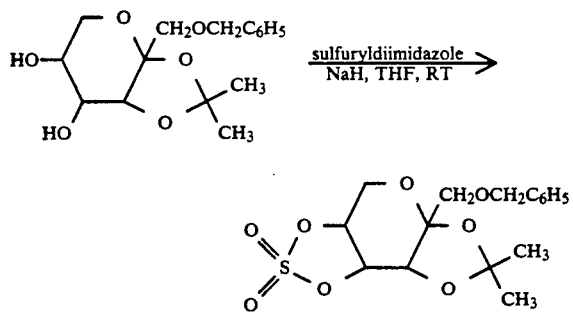

Conversion of the benzyl cyclic sulfate and diimidosulfate compounds of the formula (VII) to the corresponding cyclic sulfate compounds of formula (IIb) may be accomplished as described in the preceding method.

Cyclic sulfites and imidosulfites of formula (IIb) can also be prepared by the reaction of diols of formula (V) with thionyl chloride or NR7-substituted imidothionyl chlorides, respectively, under anhydrous conditions in aprotic solvents such as diethyl ether, dioxane, tetrahydrofuran, or in toluene or dichloromethane at about −40° C. to about 110° C., with or without the presence of a base, such as pyridine or triethylamine. For example:

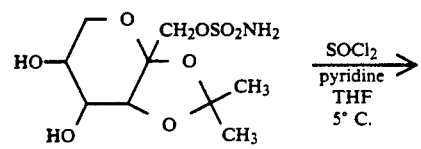

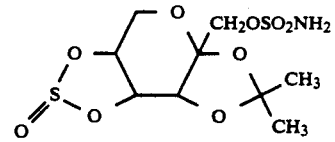

Similarly, benzyl cyclic sulfites and imidosulfites of the formula (VII) can be prepared by the reaction of diols of the formula (VIII) with thionyl chloride and NR7-substituted diimidosulfate imidothionyl chloride, respectively, in ethereal solvents such as diethyl ether, dioxane, and tetrahydrofuran or in toluene or dichloromethane at about −40° to about 110° C., with or without the presence of a base, such as pyridine or triethylamine. Oxidative debenzylation with N-bromosuccinimide according to the method of Binkley et al. in *J. Org. Chem.* 1990, 55, 378 provides the corresponding cyclic sulfites and imidosulfites of the formula (III). Conversion of these alcohols to the cyclic sulfite and imidosulfite compounds of formula (IIb) may be accomplished as previously described herein.

For example:

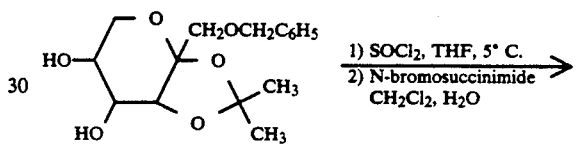

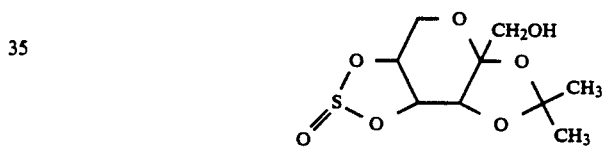

Still another method to prepare cyclic sulfates of formula (IIb) involves reaction of a triol of the formula (IX):

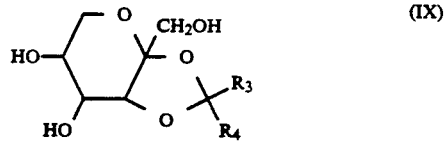

with sulfuryl chloride as described by Martin et al. in *Can. J. Chem.* 1982, 60, 1857, in an aprotic solvent such as diethyl ether, ethyl acetate, toluene or dichloromethane to produce a tris-chlorosulfate of the formula (X):

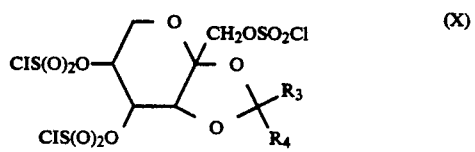

Dechlorosulfation of the tris-chlorosulfate with a base such as $K_2CO_3$, $NaHCO_3$ or pyridine at about −40° to about 25° C. in an alcohol such as methanol or ethanol gives a cyclic sulfate of formula (III), which may be converted to the corresponding compounds of formula (IIb) as previously described herein. For example:

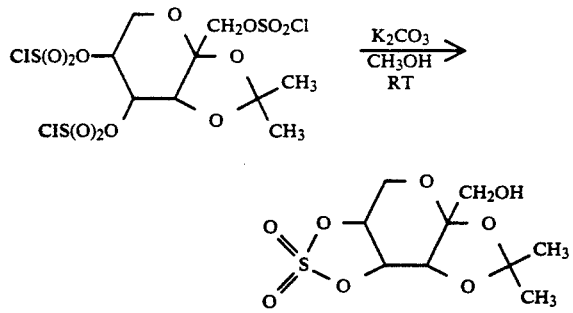

The starting materials required to synthesize compounds of formula (IIb) may be prepared by methods known to those skilled in the art of organic synthesis. For example, novel compounds of the formulas (III) and (X) may be obtained by the methods analogous to those described by Martin et al. in *Can. J. Chem.* 1982, 60, 1857. Novel diols of the formula (V) may be prepared by the procedures analogous to those described by Maryanoff et al. in *J. Med. Chem.* 1987, 30, 880. Triols of the formula (IX) may be obtained as described by the method of Wolfrom et al. in *J. Am. Chem. Soc.* 1950, 72, 4544. Diols of the formula (VIII) may be prepared by the method described by Zervas et al. in *Chem. Ber.* 1933, 66, 1698. The requisite $NR_7$-substituted imidothionyl chlorides and $NR_7$-substituted diimidosulfuryl fluorides may be prepared by the procedures analogous to those described by Levchenko et al. in *Zh. Org. Khim.* 1979, 15, 2485 and Glemser et al. in *Angew. Chem. Int. Ed. Engl.* 1980, 19, 408, respectively. The starting 2,3:4,5-bis-O-(alkylidene)-β-D-fructopyranoses and 2,3:4,5-bis-O-(cycloalkylidene)-β-D-fructopyranoses may be prepared by the method reported by Brady in *Carbohydr. Res.* 1970, 15, 35 or by the procedure described in U.S. Pat. No. 4,659,809.

The compounds of formula (I) are particularly useful as anticonvulsant agents in mammals including humans in that they result in active agents when the imidate group is removed in vivo. The anticonvulsant activity of the subject compounds was determined using a standard "maximal electroshock test" (MES). In this test, activity is indicated by a block of the toxic extensor seizure caused by application of an electric shock to mice via corneal electrodes, as described by Swinyard et al. in *J. Pharmacol. Expt. Ther.* 1952, 106, 319, and recorded as % block. A more recent description of current anticonvulsant drug screening is given by Swinyard in *Epilepsia* 1978, 19, 409. The anticonvulsant activity of the compounds of this invention tested according to the Swinyard 1952 method is shown in the following Table I.

In the test, albino male CRS-CD1 mice weighing between 18-25 g were used in all experiments (obtained from Charles River). They were allowed food and water ad libitum and were used only once. The electroshock apparatus and the corneal electrodes were purchased from Wahlquist Instrument Company, Salt Lake City, Utah.

Maximal electroshock seizures were induced by the delivery of a 60 Hertz (Hz) current of 50 milliamps (mA) intensity to the mouse through corneal electrodes for 0.2 seconds as originally described by Swinyard et al. (1952). This stimulus intensity is approximately 4 to 6 times the current producing 100% tonic extensor convulsions. During the validation of the MES test, the duration of the various seizure components following maximal electroshock were measured as follows: hindleg tonic flexion was measured from the time of the application of the stimulus to the time of onset of hindleg tonic extension (i.e. when the hindlegs deviate by greater than an angle of 90° from the torso), hindleg tonic extensor was measured from the time of extensor thrust to the onset of generalized clonus, and terminal clonus was measured from the beginning to the end of bilateral rhythmic clonic jerking. Mortality was also recorded. The duration of each seizure component agreed well with the values previously reported by Tedeschi et al. in *J. Pharmacol. Expt. Ther.* 1955, 116, 107. The corneal electrodes were concave so that saline could be applied to the electrodes to reduce mortality. If this procedure is followed, mortality should always be less than 40% in control mice. Thus, at an electroshock stimulus of 60 Hz, 50 mA and 0.2 seconds duration, the order of convulsive components and the percentage of control animals displaying the behaviors should be as follows: tonic flexion (100%), tonic extension (100%) and clonus (100%) with less than 40% mortality.

For testing compounds, the abolition of the tonic extensor component was the endpoint. Animals were dosed orally (PO) with either vehicle or test drug and at a specified time were given a maximal electric shock through corneal electrodes blotted with saline (as described above). A minimum of 10 animals were used per group and the percentage of animals in the group without tonic hindlimb extension recorded. Determination of $ED_{50}$ values (that dose of drug inhibiting 50% of the tonic extensor seizures) is shown below in Table I.

TABLE I

ACTIVITY DATA

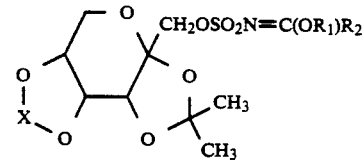

| Example | $R_1$ | $R_2$ | X | dose (mg/kg, p.o.) | MES Test (mice) % Block at 4 h |
|---|---|---|---|---|---|
| 1 | Me | Ph | $CMe_2$ | 300 | 70% |
| 2 | Et | Me | $CMe_2$ | 75 | 50% |
| 3 | Me | H | $CMe_2$ | 75 | 60% |
| 4 | Et | H | $CMe_2$ | 75 | 60% |
| 5 | Me | OMe | $CMe_2$ | 300 | 80% |
| 6 | Et | OEt | $CMe_2$ | 300 | 40% |
| 7 | Me | Ph | $SO_2$ | 75 | 100% |
| 8 | Me | Me | $SO_2$ | 75 | 90% |

Me is methyl, Et is ethyl and Ph is Phenyl

For treating epilepsy, a compound of formula (I) may be employed at a daily dosage in the range of about 10 to 2000 mg, usually in 1 to 4 divided doses, for an average adult human. This translates to about 0.2-50 mg/kg/day. A unit dose would contain about 5 to 500 mg of the active ingredient.

In general, compounds of formula (I) may be used in treating epilepsy in mammals including humans in a manner similar to that used for phenytoin. Medical aspects of the treatment of epilepsy are described in greater detail by Rall and Schleifer in *Goodman and*

Gilman's *The Pharmacological Basis of Therapeutics*, 8th ed.; Goodman Gilman, A.; Rall, T. W.; Nies, A. S.; Taylor, P., Eds.; Pergamon Press: New York, 1990; pp 436–462.

The compounds of formula (I) preferably are administered in the form of a pharmaceutical composition. To prepare the pharmaceutical compositions of this invention, one or more sulfamate compounds of formula (I) are intimately admixed with a pharmaceutical carrier according to conventional pharmaceutical compounding techniques, which carrier may take a wide variety of forms depending on the form of preparation desired for administration, e.g., oral, by suppository, or parenteral. In preparing the compositions in oral dosage form, any of the usual pharmaceutical media may be employed. Thus, for liquid oral preparations, such as, for example, suspensions, elixirs and solutions, suitable carriers and additives include oils, flavoring agents, preservatives, coloring agents and the like; for solid oral preparations such as, for example, powders, capsules and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. Suppositories may be prepared, in which case cocoa butter could be used as the carrier. For parenterals, the carrier will usually comprise an oil, though other ingredients, for purposes such as aiding solubility or for preservation, may be included. Injectable suspensions may also be prepared, in which case appropriate liquid carriers, suspending agents and the like may be employed.

It is especially advantageous to formulate the aforementioned pharmaceutical compositions in unit dosage form for ease of administration and uniformity of dosage. The term "unit dosage form" as used in the specification and claims herein refers to physically discrete units suitable as unit dosages, each unit containing a predetermined quantity of active ingredient calculated to produce the desired therapeutic effect in association with the required pharmaceutical carrier.

The pharmaceutical compositions herein will contain, per dosage unit, e.g., tablet, capsule, powder, injection, teaspoonful, suppository and the like. The compositions will be administrated in amounts as previously described herein with regard to the active ingredient and to the condition being treated. The dosages, however, may be varied depending upon the requirement of the patient, the severity of the condition being treated, and the compound being employed. Determination of optimum dosages for a particular situation is within the skill of the art.

The present invention will now be described with reference to the following Examples:

EXAMPLE 1

2,3:4,5-Bis-O-(1-methylethylidene)-β-D-fructopyranose N-(phenylmethoxymethylidene)sulfamate A mixture of topiramate (3.39 g, 10 mmol), prepared by the process disclosed in U.S. Pat. No. 4,513,006 and *J. Med. Chem.* 1987, 30, 880, and 3 mL of PhC(OMe)$_3$ was heated at 120°–125° C. for 8 h. The material was chromatographed on a column of silica gel with ethyl acetate/hexanes (1:2) to give the product as a white foam that was homogeneous by TLC. Solvent was removed and the resin crystallized on standing, and it was recrystallized from ethyl acetate/hexanes to afford colorless prisms, mp 111°–112° C. Anal. Calcd for $C_{20}H_{27}NO_9S$: C, 52.51; H, 5.95; N, 3.06. Found: C, 52.45; H, 5.96, N, 3.06.

EXAMPLE 2

2,3:4,5-Bis-O-(1-methylethylidene)-β-D-fructopyranose N-(1-ethoxyethylidene)sulfamate A mixture of topiramate (3.39 g), prepared as in Example 1 and 5 mL of MeC(OEt)$_3$ was heated at reflux for 4 h. The sample was concentrated to a syrup, which was chromatographed on a Waters Prep HPLC on a column of silica gel with ethyl acetate/hexanes (1:3) to give the product as a white foam that was homogeneous by TLC. Solvent was removed to give a thick colorless syrup that crystallized on standing. It was pulverized to a white powder that was homogeneous by TLC., mp 56°–57° C. Anal. Calcd for $C_{16}H_{27}NO_9S$: C, 46.93; H, 6.65; N, 3.42. Found: C, 47.05; H, 6.68, N, 3.45.

EXAMPLE 3

2,3:4,5-Bis-O-(1-methylethylidene)-β-D-fructopyranose N-(methoxymethylidene)sulfamate A mixture of topiramate (3.39 g) prepared as in Example 1 and 10 mL of HC(OMe)$_3$ was heated at reflux for 30 h. The sample was concentrated to a syrup, which was chromatographed on a Waters Prep HPLC on a column of silica gel with ethyl acetate/hexanes (1:3) to give the product as a thick colorless syrup that was hydrolytically unstable and homogeneous by GLC. Anal. Calcd for $C_{14}H_{23}NO_9S \cdot 0.125\ CH_2Cl_2$: C, 43.28; H, 5.98; N, 3.57. Found: C, 43.18; H, 5.98, N, 3.50.

EXAMPLE 4

2,3:4,5-Bis-O-(1-methylethylidene)-β-D-fructopyranose N-(ethoxymethylidene)sulfamate A mixture of topiramate (3.39 g) prepared as in Example 1 and 8 mL of HC(OEt)$_3$ (with one drop of glacial acetic acid) was heated at reflux for 18 h. The sample was concentrated to a syrup, which was chromatographed on a Waters Prep HPLC on a column of silica gel with ethyl acetate/hexanes (1:4) to give the product as a light tan syrup that was hydrolytically unstable. Anal. Calcd for $C_{15}H_{25}NO_9S$: C, 45.56; H, 6.37; N, 3.54. Found: C, 45.26; H, 6.17, N, 3.46.

EXAMPLE 5

2,3:4,5-Bis-O-(1-methylethylidene)-β-D-fructopyranose N-(dimethoxymethylidene)sulfamate A mixture of topiramate (3.39 g) prepared as in Example 1, 5 mL of C(OMe)$_4$, two drops of glacial acetic acid, and 20 mL of xylenes were heated at reflux for 8 h. The sample was concentrated to a syrup, which was chromatographed on a Waters Prep HPLC on a column of silica gel with ethyl acetate/hexanes (1:2) to give the product as an oil that crystallized. Recrystallization from ether/methanol (95:5) afforded white crystals, mp 123°–125° C. Anal. Calcd for $C_{15}H_{25}NO_{10}S$: C, 43.79; H, 6.12; N, 3.40. Found: C, 43.75; H, 5.96, N, 3.43.

EXAMPLE 6

2,3:4,5-Bis-O-(1-methylethylidene)-β-D-fructopyranose N-(disethoxymethylidene)sulfamate A mixture of topiramate (3.39 g) prepared as in Example 1, 5 mL of C(OEt)$_4$, two drops of glacial acetic acid, and 20 mL of xylenes was heated at reflux for 12 h. The sample was concentrated to a syrup, which was chromatographed on a Waters Prep HPLC on a column of silica gel with ethyl acetate/hexanes (1:3) to give the product as a colorless viscous syrup. Anal. Calcd for C$_{17}$H$_{29}$NO$_{10}$S•0.1 H$_2$O: C, 46.27; H, 6.67; N, 3.17. Found: C, 45.93; H, 6.48, N, 3.08.

EXAMPLE 7

2,3-O-(1-Methylethylidene)-4,5-O-sulfonyl-β-D-fructopyranose N-(Phenylmethoxymethylidene) sulfamate A mixture of 2,3-O-(1-methylethylidene)-4,5-O-sulfonyl-β-D-fructopyranose sulfamate (2.0 g) and 3.3 g of PhC(OMe)$_3$ was heated at 120° C. for 8 h. The material was chromatographed on a column of silica gel with ethyl acetate/hexanes (30:70) to give the product as a white foam that was homogeneous by TLC. Anal. Calcd for C$_{17}$H$_{21}$NO$_{11}$S$_2$: C, 42.59; H, 4.41; N, 2.92, S, 13.37. Found: C, 42.54; H, 4.27, N, 3.04; S, 13.88. The 2,3-O-(1-methylethylidene)-4,5-O-sulfonyl-β-D-fructopyranose sulfamate used hereinabove was prepared as follows:

A 3 L three-necked flask was equipped with a mechanical stirrer, thermometer, addition funnel, and an argon inlet. 2,3-O-(1-Methylethylidene)-β-D-fructopyranose sulfamate (50.0 g, 0.167 mol) was combined with ethyl acetate (1.7 L) and pyridine (31.7 g, 0.401 mol). This mixture was heated at reflux while stirring under argon to effect solution and cooled to −60° C. with a dry ice/isopropanol bath. Sulfuryl chloride (49.6 g, 0.370 mol) was added dropwise over 45 min at −60° to −50° C. while stirring under argon. The resulting white slurry was stirred at −60° to −50° C. for 1 hr, then at RT for 2 hr, and filtered through Celite. The filtrate was extracted sequentially with saturated aqueous NaCl, 1N HCl, saturated aqueous NaHCO$_3$ (twice), saturated aqueous NaCl, dried over anhydrous MgSO$_4$, filtered through Celite and concentrated in vacuo at 40° C. to furnish 85.6 g (103%) of 4,5-bis-O-chlorosulfonyl-2,3-O-(1-methylethylidene)-β-D-fructopyranose sulfamate as a white crystalline solid, which was used without further purification. An analytical sample was purified by column chromatography (CH$_2$Cl$_2$/ethyl acetate; 95:5 v/v on silica gel), mp 119°–121° C. (decomp.).

A solution of 4,5-bis-O-chlorosulfonyl-2,3-O-(1-methylethylidene)-β-D-fructopyranose sulfamate (83.1 g, 0.167 mol) in 418 mL of methanol was combined with NaHCO$_3$ (84.2 g, 1.00 mol) at RT in a 2 L three-necked flask equipped with a mechanical stirrer and an argon inlet. This mixture was stirred at RT under argon for 18 hr, filtered through Celite and concentrated in vacuo at 40° C. The residue was dissolved in ethyl acetate and extracted twice with saturated aqueous NaCl, dried over anhydrous MgSO$_4$, filtered through Celite and concentrated in vacuo at 40° C. to afford 59.3 g (98%) of product as an oil which crystallized on standing. This material was chromatographed on silica gel eluting with CH$_2$Cl$_2$/ethyl acetate (9:1 v/v on silica gel) to furnish 36.6 g (53%) of product. The chromatographed product (36.6 g) was dissolved in anhydrous ethanol (total volume=150 mL), filtered through Celite, diluted to 350 mL with water, seeded and allowed to recrystallize at 5° C. The resulting white crystals were washed with a cold mixture of ethanol/water (1:1), then with water and dried in vacuo at 40° C. (18 h) to give 31.4 g of pure 2,3-O-(1-methylethylidene)-4,5-O-sulfonyl-β-D-fructopyranose sulfamate, mp 139°–141° C. (decomp.); $[\alpha]_D^{25} = -28.8°$ (c=1.17, CH$_3$OH). Anal. Calcd. for C$_9$H$_{15}$NO$_{10}$S$_2$: C, 29.92; H, 4.18; N, 3.88. Found: C, 30.01; H, 4.36; N, 3.80.

EXAMPLE 8

2,3-O-(1-Methylethylidene)-4,5-O-sulfonyl-β-D-fructopyranose N-(Methoxyethylidene)sulfamate A mixture of 2,3-O-(1-methylethylidene)-4,5-O-sulfonyl-β-D-fructopyranose sulfamate (2.0 g) prepared as in Example 7 and 10 mL of MeC(OMe)$_3$ was heated at 90° C. for 3.5 h. The sample was concentrated to a syrup, which was chromatographed on a Waters Prep HPLC on a column of silica gel with ethyl acetate/hexanes (1:4) to give the product as an oil that crystallized on standing to a white solid, mp 89°–92° C. Anal. Calcd for C$_{12}$H$_{19}$NO$_{11}$S$_2$: C, 34.53; H, 4.59; N, 3.36; S, 15.36. Found: C, 34.58; H, 4.54, N, 3.41; S, 15.44.

What is claimed is:

1. A compound of the formula (I):

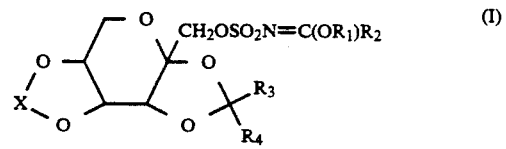

wherein R$_1$ is selected from any of C$_1$–C$_{10}$ alkyl or C$_3$–C$_{10}$ cycloalkyl;

wherein R$_2$ is selected from any of H, C$_1$–C$_{10}$ alkyl, C$_1$–C$_6$ alkoxy, C$_3$–C$_{10}$ cycloalkyl, or phenyl;

wherein R$_3$ and R$_4$ are the same or different and are selected from any of H, C$_1$–C$_6$ alkyl, or are taken together to form a cyclopentyl or cyclohexyl ring;

wherein X is CR$_5$R$_6$, wherein R$_5$ and R$_6$ are the same or different and are selected from any of H, C$_1$–C$_6$ alkyl, C$_1$–C$_4$ perfluoroalkyl, or are taken together to form a cyclopentyl or cyclohexyl ring; and a pharmaceutically acceptable salt thereof.

2. The compound of claim 1, wherein R$_3$ and R$_4$ are either H or C$_1$–C$_2$ alkyl.

3. The compound of claim 2, wherein R$_3$ and R$_4$ are both methyl.

4. The compound of claim 1, wherein X is CR$_5$R$_6$ and R$_5$ and R$_6$ are either H or C$_1$–C$_2$ alkyl.

5. The compound of claim 1, wherein R$_3$ and R$_4$ are either H or C$_1$–C$_2$ alkyl, X is CR$_5$R$_6$, and R$_5$ and R$_6$ are either H or C$_1$–C$_2$ alkyl.

6. The compound of claim 1, wherein X is C(CH$_3$)$_2$.

7. The compound of claim 6, wherein R$_1$ is methyl and R$_2$ is phenyl.

8. The compound of claim 6, wherein R$_1$ is ethyl and R$_2$ is methyl.

9. The compound of claim 6, wherein R$_1$ is methyl and R$_2$ is H.

10. The compound of claim 6, wherein R$_1$ is ethyl and R$_2$ is H.

11. The compound of claim 6, wherein R$_1$ is methyl and R$_2$ is methoxy.

12. The compound of claim 6, wherein R$_1$ is ethyl and R$_2$ is ethoxy.

13. A pharmaceutical composition for treating epilepsy comprising the compound of claim 1 in combination with a pharmaceutically acceptable carrier, the compound of claim 1 being present in therapeutically effective amount.

14. A method for treating convulsions comprising administering to an animal suffering from convulsions the compound of claim 1 in an amount sufficient to treat the convulsions.

* * * * *